United States Patent [19]

McGredy

[11] Plant 4,309

[45] Sep. 26, 1978

[54] ROSE PLANT

[76] Inventor: Samuel D. McGredy, P.O. Box 14-100, Auckland, New Zealand

[21] Appl. No.: 854,512

[22] Filed: Nov. 25, 1977

[51] Int. Cl.[2] ..... A01H 5/00

[52] U.S. Cl. ..... Plt./16

[58] Field of Search ..... Plt./11, 16–17

*Primary Examiner*—Robert E. Bagwill

*Attorney, Agent, or Firm*—Vincent G. Gioia

[57] ABSTRACT

A novel rose variety of the hybrid tea class characterized by blooms of bright orange coloring and high centered form, as hereafter shown and described.

2 Drawing Figures

The present invention relates to a new and distinct variety of rose plant of the hybrid tea rose class, which was originated by my crossing as seed parent the rose known as "Bond Street" and the rose known as "Peer Gynt" as pollen parent.

Among the novel characteristics possessed by this new variety which distinguish it from its parents and all other varieties of which I am aware are: (1) blooms of persistent orange blend coloring displaying a brilliant orange tonality from a distance and developing soft salmon general tonality on aging, (2) high centered flowers borne primarily singly to a stem in a manner typical of hybrid tea plants, (3) flowers of many petals displaying high centered, spiral form, and (4) long lasting blooms on the plant and after cutting. Asexual reproduction by budding of the new variety as performed in Clackamas County, Oreg., shows that the foregoing and other distinguishing characteristics come true to form and are established and transmitted through succeeding propagations.

The accompanying drawing shows typical specimens of the vegatative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "40C" is plate 40C of the Royal Horticultural Society Color Chart.

Parentage: Seedling.

*Seed parent.*—"Bond Street".

*Pollen parent.*—"Peer Gynt".

Class: hybrid tea.

The following observations are made of specimens grown outdoors in Clackamas County, Oreg. during the month of October.

FLOWER

Blooming habit: Continuous.

A. *Bud.*—(1) Size: Medium. (2) Form: High center. (3) Color: When sepals first divide — 40C. When petals begin to unfurl — 24B edged with 32B. When half-blown — 28B. Reverse side of petals — 24C edged with 32B. (4) Sepals: Simple, long, pointed, 144A outside with Scattered reddish glandular hairs (145A), inside densely hirsute. (5)

Peduncle: Length — long. Aspect — straight, upright. Strength — strong. Color — 144A flushed with 172B on the sunny side.

B. *Bloom.*—(1) Size: Average size when fully expanded — about 4-inches. (2) Borne: Primarily singly, if side buds present, often vegetative. (3) Form: High centered blooms, becoming flat upon opening, petals remaining at first loosely rolled outward, petals roll downward at maturity. (4) Petalage: Number of petals under normal conditions — about 36 to 40. (5) Color: (during first 2 days) Inner petals at center of flower — 28B. Outer petals — base color 30C with overlay of reddish tones over orange. Base of petals (point of attachment) 23B. Reverse of petals — 23B. General tonality from a distance — brilliant orange. (6) Color change: As bloom ages — center rows of petals 32B, and on aging, displays a soft salmon orange general tonality with little further fading.

C. *Petals.*—(1) Texture: Thick, rigid. (2) Appearance: Inside — satiny, flat texture on reverse. (3) Form: Broad, obovate. (4) Arrangement: Regularly arranged. (5) Petaloids in center: Few. (6) Persistance: Drop off cleanly. (7) Fragrance: Pronounced fruity fragrance. (8) Lasting quality: Very long lasting on plant and as cut flower.

REPRODUCTIVE ORGANS

A. Stamens, filaments and anthers:

(1) *Arrangement.*—Regularly arranged, uneven length, incurved.

(2) *Color.*—14B.

B. Pollen: Color — 14A.

C. Styles: Long, slender, hirsute.

D. Stigmas: Color — 30A, stigmatic surface — 14C.

E. Hips:

*Shape.*—Globular, sepals persist.

*Size.*—Medium.

*Color.*—153D (mature).

*Do seeds protrude?.*—Slightly, seeds large.

PLANT

A. Form: Upright growing.

B. Growth: Very vigorous, free branching. Height attained — 5½ feet.

C. Foliage: Compound 5 to 7 leaflets, noticeable proportion of 7-leaflet leaves.

(1) *Size.*—Large.

(2) *Quantity.*—Abundant.

(3) *Color.*—New foliage: Upper side — near to 79A. Under side — near to 72A. Old foliage: Upper side — 139A. Under side — 139A.

(4) *Shape.*—Elliptic, acuminate.

(5) *Texture.*—Upper side is leathery and under side is smooth.

(6) *Edge.*—Serrated.

(7) *Serration.*—Regular, dentate.

(8) *Leaf stem.*—Color — near to 172A. Under side — 139D, few thorns on rachis.

(9) *Stipules.*—Medium length, bearded, pointed and edged with reddish glandular hairs.

(10) *Resistance to disease.*—Blackspot — excellent. Mildew — Average (susceptible in fall). Rust — excellent.

D. Wood:

(1) *New wood.*—Color — near 60A. Bark — smooth, waxy.

(2) Old wood.—Color — near 146A. Bark — smooth, lusterous.

E. Thorns:

(1) *Thorns.*—Quantity (main stalk): ordinary, regularly spaced. On laterals from stalk — few just below node. Form — flat base, long pointed. Length — medium. Color — 42A. Position — regular.

(2) *Prickles.*—None.

F. Winter hardiness: Good winter hardiness.

I claim:

1. A new and distinct variety of rose plant of the hybrid tea class, substantially as shown and described, characterized particularly by high centered, spiral flowers of persistent orange blend coloring borne primarily singly to a stem which display a brilliant orange to salmon orange general tonality upon aging and are long lasting on the plant and as cut flowers grown on a very vigorous upright growing, free branching plant with large abundant foliage.

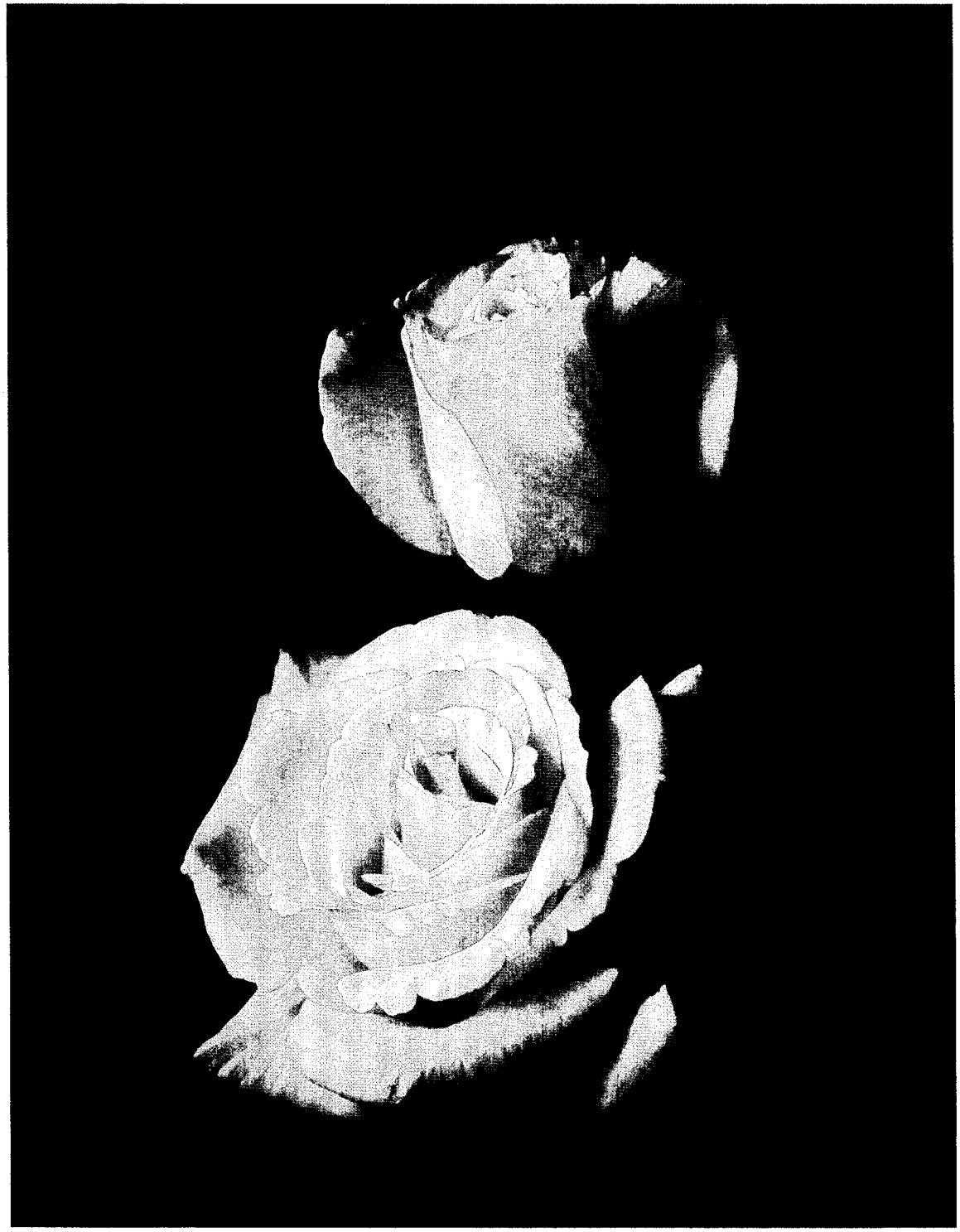

* * * * *